(12) United States Patent
Takahashi et al.

(10) Patent No.: US 8,568,552 B2
(45) Date of Patent: Oct. 29, 2013

(54) SHEET MEMBER AND METHOD OF MANUFACTURING SHEET MEMBER

(75) Inventors: Yuki Takahashi, Mima-gun (JP); Kazuya Maruhata, Mima-gun (JP)

(73) Assignee: Livedo Corporation, Ehime (JP)

( * ) Notice: Subject to any disclaimer, the term of this patent is extended or adjusted under 35 U.S.C. 154(b) by 44 days.

(21) Appl. No.: 13/331,624

(22) Filed: Dec. 20, 2011

(65) Prior Publication Data
US 2012/0125533 A1    May 24, 2012

Related U.S. Application Data

(62) Division of application No. 12/888,772, filed on Sep. 23, 2010.

(30) Foreign Application Priority Data

Sep. 25, 2009   (JP) .............................. P2009-220728

(51) Int. Cl.
- *B29C 65/00* (2006.01)
- *B32B 37/00* (2006.01)
- *B32B 7/14* (2006.01)
- *A61F 13/15* (2006.01)

(52) U.S. Cl.
USPC ..... 156/291; 156/73.6; 156/276; 604/385.27; 604/385.3

(58) Field of Classification Search
USPC ............ 156/60, 70, 73.6, 166, 176, 177, 178, 156/179, 182, 250, 267, 269, 276, 290, 291, 156/297, 299, 300, 301, 302, 324; 604/358, 604/385.01, 385.21, 385.22, 385.23, 604/385.24, 385.25, 385.26, 385.27, 604/385.28, 385.3; 427/207.1, 208.2
See application file for complete search history.

(56) References Cited

U.S. PATENT DOCUMENTS

| | | | |
|---|---|---|---|
| 4,949,668 A | 8/1990 | Heindel et al. | |
| 5,092,861 A | 3/1992 | Nomura et al. | |
| 2005/0137549 A1* | 6/2005 | Lindsay et al. | 604/385.01 |

FOREIGN PATENT DOCUMENTS

| | | |
|---|---|---|
| EP | 1 344 574 | 9/2003 |
| EP | 1 579 834 | 9/2005 |

(Continued)

OTHER PUBLICATIONS

European Search Report (in English language) issued Dec. 23, 2010 in corresponding European Patent Application No. 10 01 0206.

*Primary Examiner* — Philip Tucker
*Assistant Examiner* — Brian R Slawski
(74) *Attorney, Agent, or Firm* — Wenderoth, Lind & Ponack, L.L.P.

(57) ABSTRACT

In an outer covering sheet of an absorbent product, first, second and third adhesive layer elements each extending in a left-right direction are formed on a second covering sheet by spiral spray application. Each of these adhesive layer elements has wide width parts and narrow width parts which are continuous with the wide width parts, respectively. Therefore, hot melt adhesive can be stably discharged across the entire length of the adhesive layer element, unlike in the case where only wide width parts are formed intermittently. As a result, it is possible to obtain the outer covering sheet which is a sheet member having the adhesive layer elements with desired shapes where unevenness is decreased. In the absorbent product which is manufactured with use of the sheet member, the comfort level of the wearer can be prevented from decreasing due to unevenness of thickness of the adhesive layer elements.

17 Claims, 10 Drawing Sheets

(56) References Cited

FOREIGN PATENT DOCUMENTS

| JP | 61-137607 | 8/1986 |
| JP | 2-104354 | 4/1990 |
| JP | 2619595 | 6/1997 |
| JP | 2664501 | 10/1997 |
| JP | 2954624 | 9/1999 |
| JP | 2003-165173 | 6/2003 |
| JP | 2006-6741 | 1/2006 |
| JP | 2006-130042 | 5/2006 |
| WO | 2005/067846 | 7/2005 |

* cited by examiner

XI–XI

SHEET MEMBER AND METHOD OF MANUFACTURING SHEET MEMBER

This application is a divisional application of application Ser. No. 12/888,772, filed Sep. 23, 2010.

TECHNICAL FIELD

The present invention relates to a sheet member to be used for manufacturing an absorbent product and a method of manufacturing the sheet member.

BACKGROUND ART

In the manufacture of an absorbent product, an elastic member is conventionally bonded to a nonwoven fabric with hot melt adhesive or the like. For example, in an absorbent product disclosed in Japanese Patent Application Laid-Open No. 2006-130042 (Document 1), elastic members for legs are bonded to a middle part of an outer covering sheet and inner covering sheet, and hot melt adhesive is applied all over the middle part (containing areas where the elastic members for legs do not exist) in a spiral manner.

On the other hand, in Japanese Patent Publication No. 2664501 (Document 2) and Japanese Patent Publication No. 2954624 (Document 3), a technique is disclosed in which a spiral shaped adhesive is formed by applying adhesive spirally along a left-right direction of a disposable diaper in a short distance and elastic members are bonded to a nonwoven fabric with a plurality of spiral shaped adhesives arranged in a longitudinal direction of the disposable diaper.

In a disposable diaper disclosed in Japanese Utility Model Application Laid-Open No. 61-137607 (Document 4), hot melt adhesive is applied intermittently and linearly in a left-right direction at an adhesion position of elastic member for waist gathers and intermittent straight lines of the hot melt adhesive are arranged in an up-down direction, to form intermittent adhesive parts. In the disposable diaper of Document 4, clearances of the hot melt adhesive in respective intermittent straight lines (i.e., the clearances are distances of spaces where the hot melt adhesive is not applied) become larger toward a waist opening.

Japanese Patent Publication No. 2619595 (Document 5) discloses an apparatus for manufacturing an absorbent product. In a curtain coater thereof for discharging hot melt adhesive in curtain-like form, the hot melt adhesive is intermittently discharged from a plurality of outlets arranged so as to lie across a sheet and therefore the hot melt adhesive is applied only onto positions on the sheet where elastic members are to be bonded.

In the absorbent product of Document 1, since the hot melt adhesive is uniformly applied over a wide area, the amount of hot melt adhesive is large and the manufacturing cost of the absorbent product increases. Also there is a limit to improve the softness of the absorbent product.

On the other hand, in the disposable diapers of Documents 2 to 5, when adhesive is applied, the steps of discharging the adhesive from a nozzle for a short time, stoppage of discharging, and discharging the adhesive for a short time are repeated. Thus, application control of the adhesive is complicated. In addition, since it is difficult to discharge the adhesive stably just after start of discharging, a lump of adhesive falls at a starting end of spiral shaped adhesive and so on, which causes unevenness (i.e., mura) of adhesive.

SUMMARY OF INVENTION

The present invention is intended for a sheet member to be used for manufacturing an absorbent product. It is an object of the present invention to obtain such a sheet member having an adhesive layer element where unevenness is suppressed.

The sheet member according to the present invention comprises: a sheet; and an adhesive layer element lying on the sheet and extending in a first direction; wherein the adhesive layer element comprises: a wide width part which is formed by applying string-like adhesive onto the sheet along the first direction with vibration of the adhesive in a second direction orthogonal to the first direction; and a narrow width part which is narrower than the wide width part and which is formed by applying the string-like adhesive onto the sheet along the first direction with or without vibration of the adhesive in the second direction, the narrow width part being continuous with the wide width part.

In the present invention, it is possible to obtain the sheet member having the adhesive layer element where unevenness is suppressed.

According to a preferred embodiment of the present invention, the narrow width part has a linear shape extending in the first direction. Therefore, a difference in width between the wide width part and the narrow width part can be large, and breathability and softness of the sheet member can be increased.

According to another preferred embodiment of the present invention, the adhesive layer element comprises a plurality of wide width parts and a plurality of narrow width parts which are arranged in the first direction alternately and continuously. Therefore, areas on which the adhesive layer element is not formed are located almost evenly on the sheet member. As the result, breathability and softness of the sheet member are increased almost uniformly.

In this case, according to an aspect of the present invention, a width of each wide width part and each narrow width part gradually changes along the first direction, and a plurality of rhombus patterns are arranged along the first direction in the adhesive layer element. According to another aspect of the present invention, the sheet member further comprises another adhesive layer element which has the same structure as the adhesive layer element, extending in the first direction and being adjacent to the adhesive layer element in the second direction. Preferably, the plurality of wide width parts in the adhesive layer element are adjacent to a plurality of narrow width parts in the another adhesive layer element in the second direction, respectively, and the plurality of narrow width parts in the adhesive layer element are adjacent to a plurality of wide width parts in the another adhesive layer element in the second direction, respectively. As the result, breathability and softness of the sheet member are increased more uniformly.

According to still another preferred embodiment of the present invention, the sheet member further comprises another sheet which is bonded to the sheet with the adhesive layer element. In this case, preferably, the sheet member further comprises an elastic member which is located between the sheet and the another sheet and which is bonded to the sheet and the another sheet with the adhesive layer element. More preferably, the wide width part of the adhesive layer element is located on an area where the elastic member exists and the narrow width part is located on an area where the elastic member does not exist. In this sheet, the elastic member can be firmly bonded to the sheet and the another sheet.

In the case where the sheet member comprises the another adhesive layer element, the sheet member may further comprise: another sheet which is bonded to the sheet with the adhesive layer element and the another adhesive layer element; and super absorbent polymers or super absorbent fibers which lie between the sheet and the another sheet, and which are located at least at an area between the adhesive layer element and the another adhesive layer element. It is therefore possible to easily deform the sheet member having the super absorbent polymers or the super absorbent fibers.

Preferable adhesive layer element is formed by spiral spray application.

The present invention is also intended for a method of manufacturing a sheet member to be used for manufacturing an absorbent product. The method of manufacturing a sheet member according to the present invention comprises the steps of: a) preparing a sheet; and b) forming an adhesive layer element lying on the sheet and extending in a first direction; wherein the step b) comprises the steps of: b1) forming a wide width part by applying string-like adhesive onto the sheet along the first direction with vibration of the adhesive in a second direction orthogonal to the first direction; and b2) forming a narrow width part which is narrower than the wide width part, by applying the string-like adhesive onto the sheet along the first direction with or without vibration of the adhesive in the second direction, the narrow width part being continuous with the wide width part.

These and other objects, features, aspects and advantages of the present invention will become more apparent from the following detailed description of the present invention when taken in conjunction with the accompanying drawings.

DESCRIPTION OF EMBODIMENTS

Figure 1:
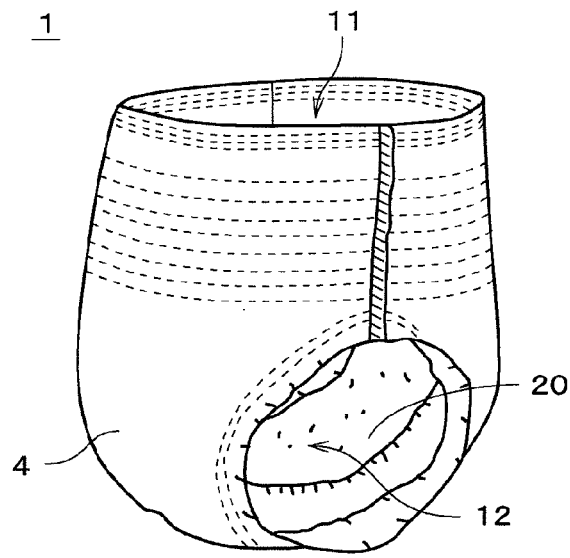
FIG. 1 is a perspective view showing an appearance of an absorbent product in accordance with a first preferred embodiment.

FIG. 1 is a perspective view showing an appearance of an absorbent product 1 comprising an outer covering sheet which is a sheet member in accordance with a first preferred embodiment of the present invention. As shown in FIG. 1, the absorbent product 1 is a pants-type (i.e., pull-up type) disposable diaper which has a waist opening 11 at an upper end being an end on the upper side of FIG. 1 and a pair of leg openings 12 on a lower part, and it receives excrement from a wearer.

Figure 2:
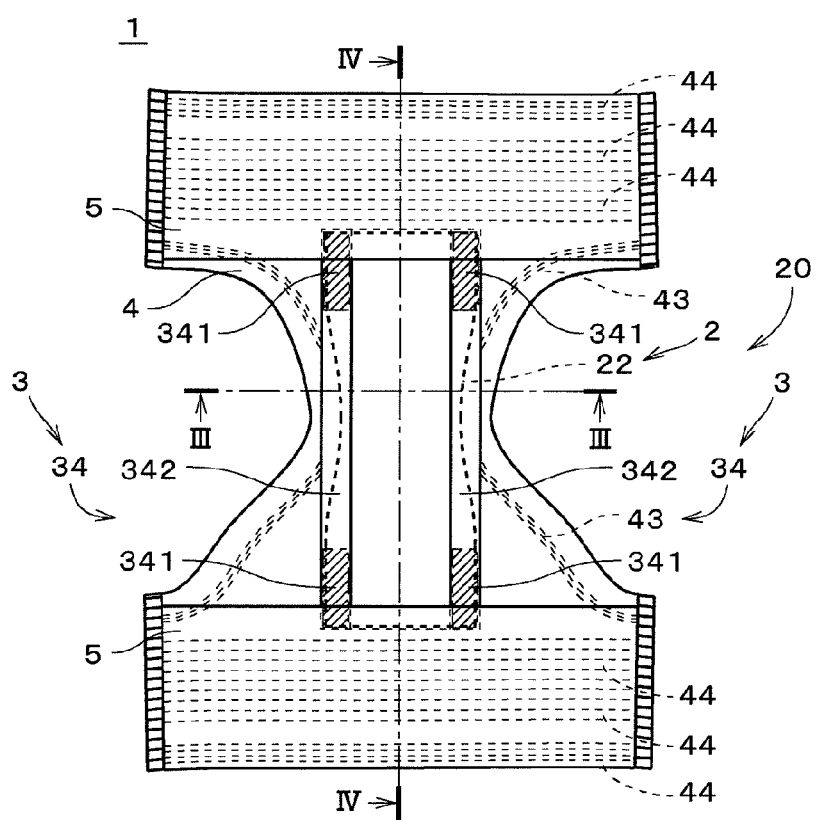
FIG. 2 is a plan view of the absorbent product in a state where the absorbent product is developed.

FIG. 2 is a plan view of the absorbent product 1 in a state where the absorbent product 1 is developed and in FIG. 2, the absorbent product 1 is viewed from the wearer's side. As shown in FIG. 2, the absorbent product 1 has an outer covering sheet 4, a sheet-like absorber 20 which is attached on the outer covering sheet 4 to absorb excrement from the wearer (i.e., the absorber 20 is located on the wearer's side of the outer covering sheet 4), and two end holding sheets 5 which are bonded to the outer covering sheet 4 at both ends of absorber 20 in its longitudinal direction (i.e., an up-down direction in FIG. 2). Each end portion of absorber 20 in the longitudinal direction is caught between the end holding sheet 5 and the outer covering sheet 4 to be fixed.

In the absorbent product 1, an upper portion in FIG. 2 is to be positioned on the front side (stomach side) of the wearer, and a lower portion in FIG. 2 is to be positioned on the back side of the wearer. In the following description, the portions of the absorbent product 1 which are to be positioned on the front side and the back side of the wearer are referred to as a "front part" and a "back part", respectively, and a portion to face a crotch region of the wearer at a position between the front part and the back part is referred to as a "middle part".

As shown in FIG. 1, in the absorbent product 1, the outer covering sheet 4 is folded at the middle part together with the absorber 20. In the state where the middle part is located on the downside, left and right ends of the front part (i.e., both ends in a left-right direction orthogonal to the longitudinal direction) are bonded to left and right ends of the back part, respectively. Therefore, the waist opening 11 is formed at upper ends of the front part and the back part, and on the downside of the front part and the back part, the pair of leg openings 12 is formed on left and right sides of the middle part, to thereby form the absorbent product 1 in a shape of underpants.

Figure 3:
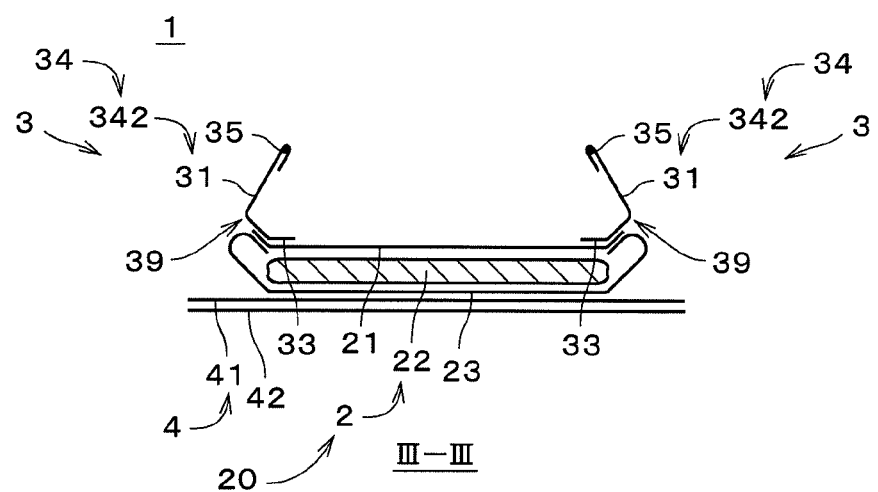
FIGS. 3 and 4 are cross-sectional views of the absorbent product.

FIG. 3 is a cross-sectional view of the absorbent product 1 taken along a line III-III in FIG. 2 (i.e., a cross-sectional view at the middle part). In FIG. 3, respective constituents of the absorbent product 1 are drawn to be slightly apart from one another for easy understanding of the drawing (the same applies to FIG. 4). The absorber 20 has a sheet-like main body part 2 and a pair of side sheets 3 located on both side portions of the main body part 2 (i.e., both sides of the main body part 2 in the left-right direction), and the pair of side sheets 3 extends across almost the entire length of the main body part 2 in the longitudinal direction. The main body part 2 has a top sheet 21, a back sheet 23 and an absorbent core 22 which is located between the top sheet 21 and the back sheet 23. The contour of the absorbent core 22 is drawn by thick broken lines in FIG. 2 for easy understanding of the drawing. As shown in FIG. 2, a width of the absorbent core 22 at each of the two ends in the longitudinal direction is larger than that at middle in the longitudinal direction. In other words, the absorbent core 22 is formed in a form of hourglass.

As shown in FIG. 3, each side sheet 3 has a side sheet main body 31 and an elastic member 35 which is bonded to the side sheet main body 31 with hot melt adhesive or the like. The elastic member 35 is bonded to a free edge (a free end) of the side sheet main body 31 along the free edge.

As shown in FIG. 3, each of the pair of side sheets 3 has a strip-like bonded part 33 and a side wall part 34. The bonded part 33 is one of two portions divided by a folding line 39 extending across almost the entire length thereof in the longitudinal direction, and the side wall part 34 is the other of the two portions. The pair of bonded parts 33 is located in the vicinity of both side edges of the main body part 2, it lies across almost the entire length thereof in the longitudinal direction, and it is bonded on the upper side (i.e., the wearer's side) of the main body part 2 with hot melt adhesive. Each side wall part 34 is continuous from the bonded part 33 at an outside edge (i.e., an edge located on the outside in the left-right direction) of the bonded part 33 which is the folding line 39, and on the side portion of the main body part 2, it extends across almost the entire length of the main body part 2 in the longitudinal direction.

Each side wall part 34 is in touch with the bonded part 33 at both end portions thereof in the longitudinal direction, and it is fixed on the bonded part 33 by heat bonding or ultrasonic bonding. In the following description, a portion fixed on the bonded part 33 in the side wall part 34 is referred to as a "side wall end part 341". In FIG. 2, hatching lines are drawn at each side wall end part 341 of the side sheet 3 for easy understanding of the drawing. As shown in FIGS. 2 and 3, the side wall part 34 has a standing part 342 standing up from the main body part 2 at a middle portion thereof in the longitudinal direction and it is continuous from the two side wall end parts 341. In the side wall part 34, the elastic member 35 shown in FIG. 3 contracts to form gathers in the standing part 342.

Figure 4:
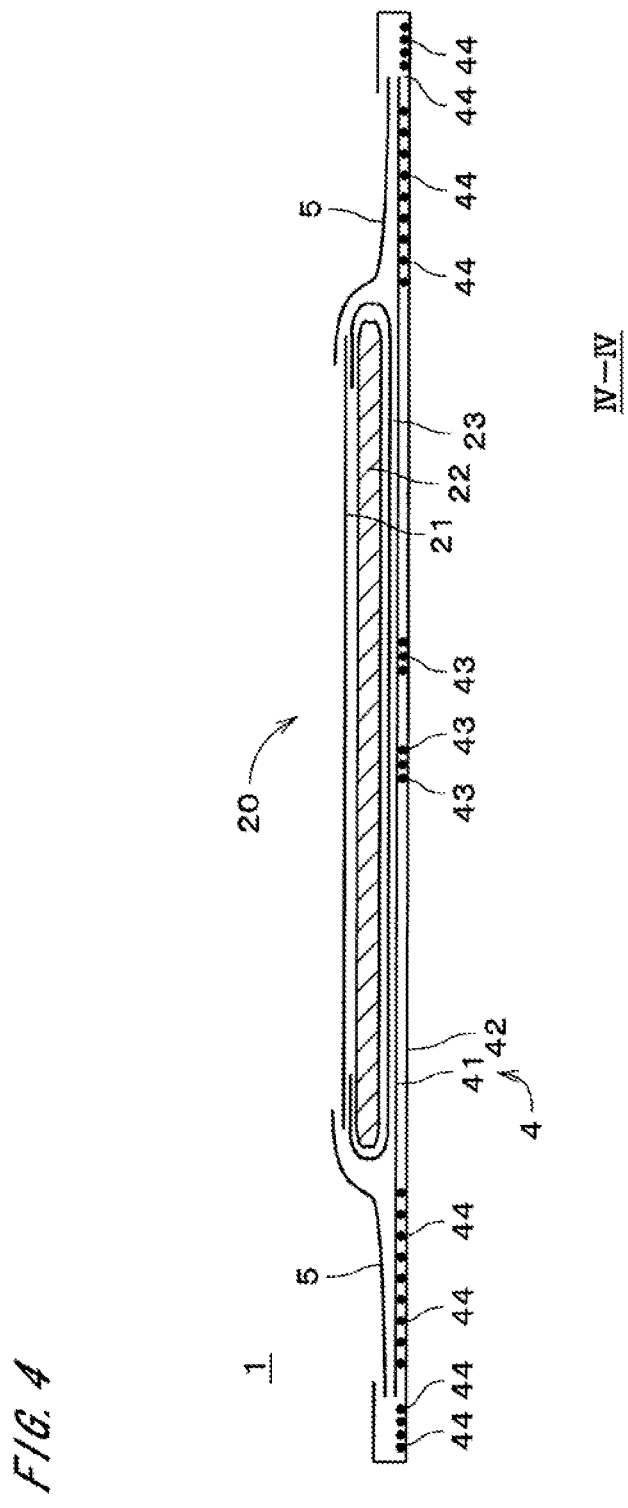

FIG. 4 is a cross-sectional view of the absorbent product 1 taken along a line IV-IV in FIG. 2. As shown in FIGS. 3 and 4, the outer covering sheet 4 has a first covering sheet 41 and a second covering sheet 42, and the second covering sheet 42 is layered on the lower side (i.e., the side not facing the wearer) of the first covering sheet 41. As shown in FIG. 4, each end of the second covering sheet 42 in the longitudinal direction is folded upward (i.e., toward the wearer) so as to be bonded on the end holding sheet 5 which is bonded on the first covering sheet 41.

The outer covering sheet 4 has a plurality of leg elastic members 43 (six leg elastic members in the present embodiment) and a plurality of waist elastic members 44 (twenty-six waist elastic members in the present embodiment), and these elastic members are located between the first covering sheet 41 and the second covering sheet 42 or two layers of the second covering sheet 42 which are formed as a double-layered structure by folding the each end in the longitudinal direction. The leg elastic members 43 and the waist elastic members 44 shown in FIGS. 2 and 4 are bonded to the first covering sheet 41 and the second covering sheet 42 with after-mentioned adhesive layer elements extending on the second covering sheet 42 in the left-right direction, in the state where each of the elastic members is stretched (i.e., the stretched leg elastic members 43 and the stretched waist elastic members 44 are bonded). The adhesive layer elements are formed of hot melt adhesive.

In the absorbent product 1, by contraction of the leg elastic members 43, the first covering sheet 41 and the second covering sheet 42 are contracted to form leg gathers. Also the waist elastic members 44 contract to form waist gathers. On the second covering sheet 42, the end holding sheets 5 and the back sheet 23 of the absorber 20 are bonded with hot melt adhesive or the like. In FIG. 4, the hot melt adhesive used for bonding of the leg elastic members 43 and bonding of the waist elastic members 44 is not shown.

The top sheet 21 shown in FIGS. 3 and 4 is a nonwoven fabric made of liquid-pervious sheet material, for example, hydrophilic fibers, and the top sheet 21 immediately catches moisture of excrement from the wearer and moves the moisture into the absorbent core 22. Examples of nonwoven fabrics used for the top sheet 21 are a point-bond nonwoven fabric, air-through nonwoven fabric, spunlace nonwoven fabric and spunbond nonwoven fabric, and as hydrophilic fibers for making these nonwoven fabrics, normally, cellulose, rayon, cotton and the like are used. As the top sheet 21, a liquid-pervious nonwoven fabric made of hydrophobic fibers (for example, polypropylene, polyethylene, polyester, polyamide or nylon) where hydrophilic treatment is performed on its surface with a surfactant may be utilized.

The absorbent core 22 is formed by wrapping a mixture of hydrophilic fibers such as crushed pulp fibers or cellulose fibers and super absorbent material such as granulated super absorbent polymers (e.g., SAP (Super Absorbent Polymer)) or super absorbent fibers in a tissue paper, a liquid-pervious nonwoven fabric or the like, and the absorbent core 22 rapidly absorbs and retains the moisture which has passed through the top sheet 21. The tissue paper, the liquid-pervious nonwoven fabric or the like to wrap the hydrophilic fibers, is bonded to the hydrophilic fibers and the absorbent material with hot melt adhesive, to prevent deformation of the hydrophilic fibers and falling of the absorbent material (especially, falling after absorption of moisture). In the present embodiment, the absorbent core 22 includes pulp fibers and SAP.

As the back sheet 23, used is a water-repellent or liquid-impervious nonwoven fabric (for example, a spunbond nonwoven fabric, meltblown nonwoven fabric or SMS (spunbond-meltblown-spunbond) nonwoven fabric) made of hydrophobic fibers, or a water-repellent or liquid-impervious plastic film. The back sheet 23 prevents moisture of excrement or the like which has come to the back sheet 23, from leaking out to the outer side of the main body part 2. In a case where a plastic film is used for the back sheet 23, it is preferable that a plastic film with permeability (breathability) is used, from the view point of preventing sweatiness in the absorbent product 1 and providing comfortable feeling to the wearer.

As the side sheet main body 31, used is a water-repellent or liquid-impervious nonwoven fabric (for example, a spunbond nonwoven fabric, meltblown nonwoven fabric or SMS nonwoven fabric) made of hydrophobic fibers. For example, a polyurethane yarn, strip-like polyurethane film, yarn-like or strip-like natural rubber, or the like is used as the elastic member 35. In the present embodiment, a polyurethane yarn is used as the elastic member 35. Similar material to the top sheet 21 or similar material to the side sheet main body 31 is used for the end holding sheets 5.

As the first covering sheet 41 and the second covering sheet 42 of the outer covering sheet 4, used is a water-repellent or liquid-impervious nonwoven fabric made of hydrophobic fibers, or a water-repellent or liquid-impervious plastic film in a similar fashion to the back sheet 23. A laminated sheet of the nonwoven fabric and the plastic film may be used. It is preferable that the plastic film has permeability (breathability). In a similar fashion to the top sheet 21, a nonwoven fabric made of hydrophilic fibers or a liquid-pervious nonwoven fabric made of hydrophobic fibers where hydrophilic treatment is performed may be utilized as the first covering sheet 41 and the second covering sheet 42. As the leg elastic member 43 and the waist elastic member 44, for example, a polyurethane yarn, strip-like polyurethane film, yarn-like or strip-like natural rubber, or the like is used in a similar fashion to the elastic member 35 of the side sheet 3. In the present embodiment, a polyurethane yarn is utilized as the leg elastic member 43 and the waist elastic member 44.

Figure 5:
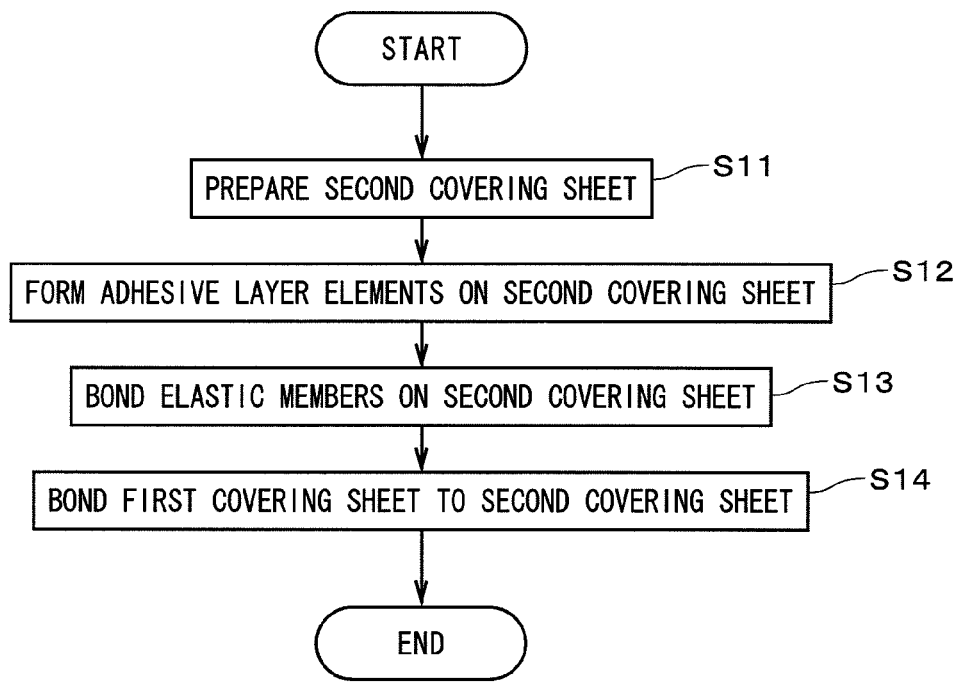
FIGS. 5 and 6 are flowcharts showing an operation flow for manufacturing an outer covering sheet.
Figure 6:
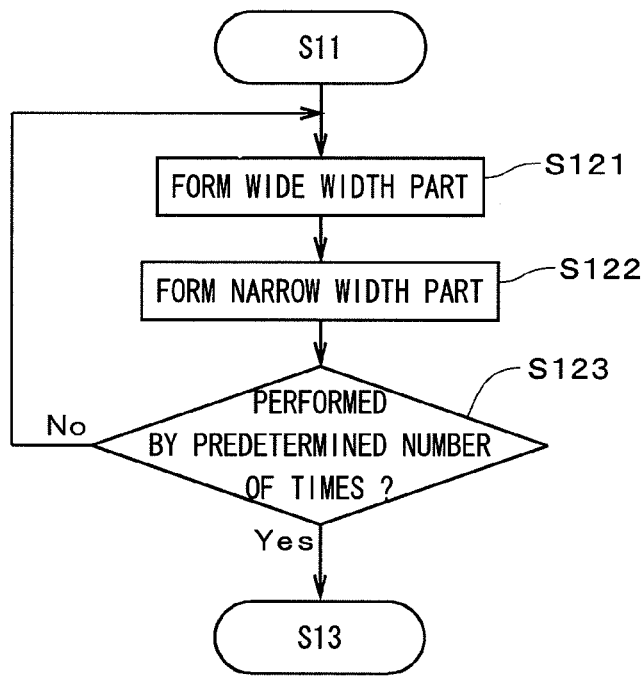
Figure 7:
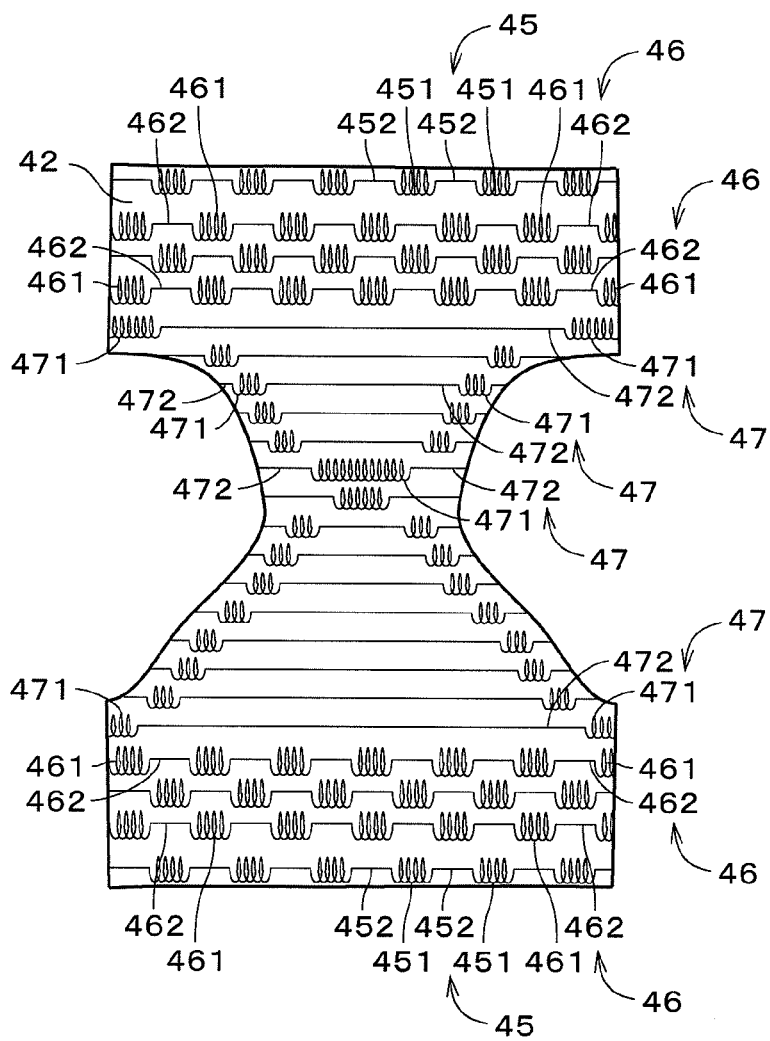
FIGS. 7 and 8 are plan views of the outer covering sheet in the course of manufacturing.
Figure 8:
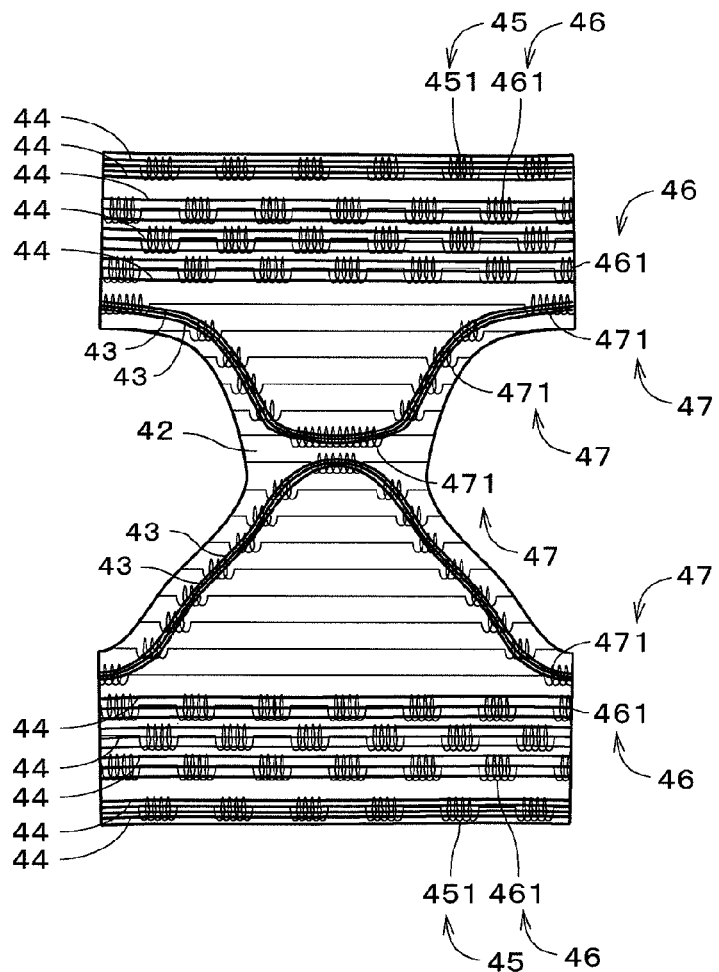

Next, discussion will be made on manufacture of the outer covering sheet 4 which is one of sheet members to be used for manufacturing the absorbent product 1. FIGS. 5 and 6 are flowcharts showing an operation flow for manufacturing the outer covering sheet 4, and FIGS. 7 and 8 are plan views showing the outer covering sheet 4 in the course of manufacturing. In the manufacture of the outer covering sheet 4, first, the second covering sheet 42 shown in FIG. 7 is prepared (Step S11). In actual manufacturing process of the outer covering sheet 4, a continuous sheet body where a plurality of second covering sheets 42 are continuous in a left-right direction (i.e., the left-right direction in FIG. 7) is prepared.

Subsequently, in an apparatus for manufacturing the absorbent product 1, string-like hot melt adhesive is discharged from each of a plurality of nozzles located above the second covering sheet 42 and arranged in the longitudinal direction orthogonal to the left-right direction (i.e., the longitudinal direction is a vertical direction in FIG. 7 and hereinafter referred to as the "vertical direction"), while the second covering sheet 42 is moved in the left-right direction. Therefore, as shown in FIG. 7, a plurality of adhesive layer elements 45, 46, 47 each extending in the left-right direction are formed on an upper surface (i.e., surface facing the wearer) of the second covering sheet 42 (Step S12). The hot melt adhesive used for formation of the adhesive layer elements 45, 46, 47 is olefin hot melt adhesive, rubber hot melt adhesive, EVA (Ethylene-Vinyl Acetate) hot melt adhesive or the like. In the present embodiment, the adhesive layer elements 45, 46, 47 are formed with rubber hot melt adhesive with high flexibility.

In the following description, the adhesive layer elements 45, 46, 47 are referred to as "first adhesive layer elements 45", "second adhesive layer elements 46" and "third adhesive layer elements 47", respectively, to distinguish one another. In the case where there is no need to distinguish the first adhesive layer elements 45, the second adhesive layer elements 46 and the third adhesive layer elements 47, they are referred to as the adhesive layer elements as a whole. In the apparatus for manufacturing the absorbent product 1 in accordance with the present embodiment, the plurality of adhesive layer elements are formed in almost parallel, however the plurality of adhesive layer elements are not necessarily formed in parallel. After one adhesive layer element out of the plurality of adhesive layer elements is formed, another adhesive layer element may be formed.

The outer covering sheet 4 has two first adhesive layer elements 45 located both end parts thereof in the vertical direction (i.e., the longitudinal direction of the second covering sheet 42), and fifteen third adhesive layer elements 47 arranged in the vertical direction and being adjacent to one another at the middle part of the second covering sheet 42 (i.e., a midportion in the vertical direction). The outer covering sheet 4 further has three second adhesive layer elements 46 arranged in the vertical direction and being adjacent to one another at an area between one first adhesive layer element 45 and the third adhesive layer element 47 nearest to the first adhesive layer element 45, and three second adhesive layer elements 46 arranged in the vertical direction and being adjacent to one another at an area between the other first adhesive layer element 45 and the third adhesive layer element 47 nearest to the first adhesive layer element 45. In other words, three second adhesive layer elements 46 are located at each of the front part and the back part in the second covering sheet 42.

Each first adhesive layer element 45 is formed by spiral spray application and has wide width parts 451 each of which is formed by applying string-like hot melt adhesive in a spiral form extending in the left-right direction, and narrow width parts 452 each of which is formed by applying the string-like hot melt adhesive in a straight line form extending in the left-right direction. The narrow width parts 452 are narrower than the wide width parts 451 with respect to the vertical direction (i.e., a width of the narrow width parts 452 in the vertical direction is smaller than that of the wide width parts 451). In the first adhesive layer element 45, the plurality of wide width parts 451 and the plurality of narrow width parts 452 are arranged in the left-right direction alternately and continuously, and a length of each wide width part 451 in the left-right direction is almost equal to a length of each narrow width parts 452 in the left-right direction.

FIG. 6 is a flowchart showing a detailed operation flow of formation of the first adhesive layer elements 45, the second adhesive layer elements 46 and the third adhesive layer elements 47 in Step S12. In the formation of each first adhesive layer element 45, while the string-like hot melt adhesive is discharged from a nozzle toward the second covering sheet 42 moving from one side to the other side in the left-right direction, the hot melt adhesive is vibrated in the left-right direction and the vertical direction so as to draw approximate circles in a planar view by controlling a direction of gas ejected from gas outlets toward the hot melt adhesive where the gas outlets are located around a discharging outlet of the nozzle, and therefore a wide width part 451 is formed (Step S121).

While the string-like hot melt adhesive is discharged from the nozzle toward the second covering sheet 42 moving as above, vibration of the hot melt adhesive in the left-right direction and the vertical direction is stopped by stopping ejection of the gas from the gas outlets (or ejecting the gas in directions where discharging the hot melt adhesive is unaffected), and therefore a narrow width part 452 is formed (Step S122).

The formation of wide width part 451 (Step S121) and the formation of narrow width part 452 (Step S122) in the first adhesive layer element 45 are performed (repeated) alternately and continuously by a predetermined number of times (Step S123), and therefore the first adhesive layer element 45 is completed. Here, if the left-right direction and the vertical direction of the absorbent product 1 are referred to as a "first direction" and a "second direction", respectively, the wide width parts 451 are formed by applying the string-like hot melt adhesive onto the second covering sheet 42 along the first direction with vibration of the hot melt adhesive in the first direction and the second direction. The narrow width parts 452 are formed by applying the string-like hot melt adhesive onto the second covering sheet 42 along the first direction without vibration of the hot melt adhesive in the second direction, and respective narrow width parts 452 are continuous with the wide width parts 451.

In the apparatus for manufacturing the absorbent product 1, an application quantity of the hot melt adhesive is controlled in Step S121 and Step S122 and therefore, an application quantity of the hot melt adhesive per unit length in the left-right direction at the wide width parts 451 is controlled so as to be more than that at the narrow width parts 452 in the formation of the first adhesive layer element 45. More specifically, application control is performed so that a ratio of the application quantity per the unit length in the left-right direction at the narrow width parts 452 to the application quantity per the unit length at the wide width parts 451 becomes equal to a ratio of an application distance per the unit length in the left-right direction at the narrow width parts 452 (the application distance is a length of trajectory of the hot melt adhesive applied in a linear form and the application distance per the unit length is equal to the unit length) to an application distance (that is a length of trajectory of the hot melt adhesive applied in a spiral form) per the unit length in the left-right direction at the wide width parts 451. Therefore, a line width of the applied hot melt adhesive is almost uniform at all portions of the wide width parts 451 and the narrow width parts 452.

In the same way as the first adhesive layer elements 45, each second adhesive layer element 46 is formed by spiral spray application and has wide width parts 461 each of which is formed by applying the string-like hot melt adhesive in a spiral form extending in the left-right direction, and narrow width parts 462 each of which is formed by applying the string-like hot melt adhesive in a straight line form extending in the left-right direction. The narrow width parts 462 are narrower than the wide width parts 461 with respect to the vertical direction. Also in the second adhesive layer element 46, the plurality of wide width parts 461 and the plurality of narrow width parts 462 which are formed by processes shown in Steps S121 to S123 are arranged in the left-right direction alternately and continuously, and formation of the wide width parts 461 and the narrow width parts 462 and control of application quantity of the hot melt adhesive in the formation of the wide width parts 461 and the narrow width parts 462 are the same as those in the above formation of the first adhesive layer elements 45.

In each second adhesive layer element 46, a length of each wide width part 461 is almost equal to a length of each narrow width part 462. In the three second adhesive layer elements 46 arranged in the vertical direction, the plurality of wide width parts 461 in one second adhesive layer element 46 are adjacent respectively, in the vertical direction, to the plurality of narrow width parts 462 in another second adhesive layer element 46 which is adjacent to the one second adhesive layer element 46. And the plurality of narrow width parts 462 in the one second adhesive layer element 46 are adjacent respectively, in the vertical direction, to the plurality of wide width parts 461 in the another second adhesive layer element 46. In other words, the wide width parts 461 and the narrow width parts 462 in the plurality of second adhesive layer elements 46 are arranged staggeringly.

In the same way as the first adhesive layer elements 45 and the second adhesive layer elements 46, each third adhesive layer element 47 is formed by spiral spray application and has wide width parts 471 each of which is formed by applying the string-like hot melt adhesive in a spiral form extending in the left-right direction, and narrow width parts 472 each of which is formed by applying the string-like hot melt adhesive in a straight line form extending in the left-right direction. The narrow width parts 472 are narrower than the wide width parts 471 with respect to the vertical direction. Also in the third adhesive layer element 47, wide width parts (or wide width part) 471 and narrow width parts (or narrow width part) 472 which are formed by processes shown in Steps S121 to S123 are arranged in the left-right direction alternately and continuously, and formation of the wide width parts 471 and the narrow width parts 472 and control of application quantity of the hot melt adhesive in the formation of the wide width parts 471 and the narrow width parts 472 are the same as those in the above formation of the first adhesive layer elements 45.

In each of the uppermost third adhesive layer element 47 and the lowermost third adhesive layer element 47 in FIG. 7, two wide width parts 471 are provided at both ends in the left-right direction, respectively, and one relatively-long narrow width part 472 is provided between the two wide width parts 471. In each of the sixth and seventh elements 47 from the uppermost third adhesive layer element 47 in FIG. 7, one relatively-long wide width part 471 is provided at almost middle in the left-right direction, and two narrow width parts 472 are provided on both left and right sides of the wide width part 471, respectively. In the other third adhesive layer elements 47, two wide width parts 471 are provided in the vicinities of both ends in the left-right direction, respectively, one relatively-long narrow width part 472 is provided between the two wide width parts 471, and one narrow width parts 472 is provided at the outside of each wide width part 471 in the left-right direction.

After the first adhesive layer elements 45, the second adhesive layer elements 46 and the third adhesive layer elements 47 are formed on the second covering sheet 42, as shown in FIG. 8, six leg elastic members 43 and twenty-six waist elastic members 44 each of which is stretched are located on the second covering sheet 42 and they are bonded with the first adhesive layer elements 45, the second adhesive layer elements 46 and the third adhesive layer elements 47 (Step S13). Three leg elastic members 43 are located along edges of the leg openings so as to be overlapped (i.e., to contact) with the wide width parts 471 of each of six third adhesive layer elements 47 located at the upper side in FIG. 8, and the three leg elastic members 43 are bonded on the second covering sheet 42 with the wide width parts 471 lying across them.

The other three leg elastic members 43 are located along edges of the leg openings so as to be overlapped (i.e., to contact) with the wide width parts 471 of each of nine third adhesive layer elements 47 located at the lower side in FIG. 8, and the three leg elastic members 43 are bonded on the second covering sheet 42 with the wide width parts 471 lying across them. In other words, the wide width parts 471 of the third adhesive layer elements 47 are located on areas where the leg elastic members 43 exist (in the present embodiment, they are located on only the areas) and the narrow width parts 472 are located on areas where the leg elastic members 43 do not exist (in the present embodiment, they are located on only the areas), in the absorbent product 1.

In the front part of the second covering sheet 42, four waist elastic members 44 are located along the upper edge of the second covering sheet 42, and the four waist elastic members 44 are bonded on the second covering sheet 42 with the first adhesive layer element 45. Each of the plurality of wide width parts 451 in the first adhesive layer element 45 lies across the four waist elastic members 44 in the vertical direction. Nine waist elastic members 44 are located almost parallel to the left-right direction and bonded on the second covering sheet 42 with the three second adhesive layer elements 46. Each of the plurality of wide width parts 461 in the second adhesive layer elements 46 lies in the vertical direction across three waist elastic members 44 being adjacent to one another.

In the back part of the second covering sheet 42, four waist elastic members 44 are located along the lower edge of the second covering sheet 42, and the four waist elastic members 44 are bonded on the second covering sheet 42 with the first adhesive layer element 45, in the same way as the front part. Each of the plurality of wide width parts 451 in the first adhesive layer element 45 lies across the four waist elastic members 44 in the vertical direction. Nine waist elastic members 44 are located almost parallel to the left-right direction and bonded on the second covering sheet 42 with the three second adhesive layer elements 46. Each of the plurality of wide width parts 461 in the second adhesive layer elements 46 lies in the vertical direction across three waist elastic members 44 being adjacent to one another.

After the leg elastic members 43 and the waist elastic members 44 are bonded on the second covering sheet 42, the first covering sheet 41 shown in FIGS. 3 and 4 (practically, a continuous sheet body where a plurality of first covering sheets 41 are continuous in the left-right direction) are overlaid on the upper surface of the second covering sheet 42 with the leg elastic members 43 and the waist elastic members 44 lying between them, the first covering sheet 41 is bonded to the second covering sheet 42 with the first adhesive layer elements 45, the second adhesive layer elements 46 and the third adhesive layer elements 47, and therefore the outer covering sheet 4 is formed (it is considered that these adhesive layer elements become one adhesive layer) (Step S14). It can be considered that Step S14 is a process where the leg elastic members 43 and the waist elastic members 44 located between the first covering sheet 41 and the second covering sheet 42, are bonded to the first covering sheet 41 and the second covering sheet 42 with the first adhesive layer elements 45, the second adhesive layer elements 46 and the third adhesive layer elements 47.

In the apparatus for manufacturing the absorbent product 1 in accordance with the present embodiment, although bonding of the first covering sheet 41 to the second covering sheet 42 (Step S14) is performed after bonding of the leg elastic members 43 and the waist elastic members 44 to the second covering sheet 42 (Step S13), Step S13 and Step S14 may be performed in parallel by locating the leg elastic members 43 and the waist elastic members 44 on the upper surface of the second covering sheet 42 in almost parallel with overlaying the first covering sheet 41 on the upper surface of the second covering sheet 42.

As described above, in the outer covering sheet 4 of the absorbent product 1, since the first adhesive layer elements 45, the second adhesive layer elements 46 and the third adhesive layer elements 47 extending in the left-right direction on the second covering sheet 42 comprise respectively the wide width parts 451, 461, 471 and the narrow width parts 452, 462, 472 which are continuous with the wide width parts 451, 461, 471, the hot melt adhesive can be stably discharged across the entire length of each adhesive layer element, unlike in the case where only wide width parts are formed intermittently (i.e., the wide width parts are isolated). Therefore, it is possible to obtain the outer covering sheet 4 which is a sheet member having the adhesive layer elements with desired shapes where unevenness is decreased (suppressed). And in the absorbent product 1 which is manufactured with use of the sheet member, comfort level of the wearer can be prevented from decreasing due to unevenness of thickness of the adhesive layer elements and so on.

In the outer covering sheet 4, since the narrow width parts 452, 462, 472 are provided to the first adhesive layer elements 45, the second adhesive layer elements 46 and the third adhesive layer elements 47, breathability and softness of the outer covering sheet 4 can be increased as compared with the case where whole the adhesive layer elements are made to be wide width parts. As the result, breathability and softness of the absorbent product 1 can be increased, and comfort level of the wearer to the absorbent product 1 can be increased. In addition, since the narrow width parts of each adhesive layer element has a linear shape extending in the left-right direction, a difference in width between the wide width parts and the narrow width parts can be large. Therefore, breathability and softness of the outer covering sheet 4 and the absorbent product 1 can be further increased. Furthermore, the plurality of wide width parts and the plurality of narrow width parts which are arranged in the left-right direction alternately and continuously are provided in the adhesive layer element. Therefore, areas on which the adhesive layer elements are not formed are located almost evenly on the second covering sheet 42. As the result, breathability and softness of the outer covering sheet 4 are increased almost uniformly.

As above, in the outer covering sheet 4, since the plurality of adhesive layer elements are adjacent to one another in the vertical direction, the adhesive layer elements can be provided over a wide area on the second covering sheet 42. Therefore, the leg elastic members 43, the waist elastic members 44 and the first covering sheet 41 are firmly bonded over the wide area on the second covering sheet 42. In two adhesive layer elements adjacent to each other, the wide width parts in one adhesive layer element are adjacent to the narrow width parts in the other adhesive layer element in the vertical direction, respectively, and the narrow width parts in the one adhesive layer element are adjacent to the wide width parts in the other adhesive layer element in the vertical direction, respectively. As the result, breathability and softness of the outer covering sheet 4 are increased more uniformly.

The outer covering sheet 4 comprises the first covering sheet 41 bonded on the second covering sheet 42. This increase tensile strength and the like of the outer covering sheet 4, and breakage of the outer covering sheet 4 by tension is suppressed when wearing the absorbent product 1 or the like. Since the leg elastic members 43 and the waist elastic members 44 are bonded between the first covering sheet 41 and the second covering sheet 42, stretchability can be given to the outer covering sheet 4 easily. Furthermore, the wide width parts 471 of the third adhesive layer elements 47 are located on areas where the leg elastic members 43 exist, and the narrow width parts 472 are located on areas where the leg elastic members 43 do not exist (i.e., the areas are nonexistent areas). Therefore, the leg elastic members 43 can be firmly bonded to the first covering sheet 41 and the second covering sheet 42, and breathability and softness of areas on which the leg elastic members 43 need not be bonded (i.e., each of the areas is located between a left side portion and a right side portion of the almost U-shaped leg elastic members 43) can be increased. In the outer covering sheet 4, the plurality of leg elastic members 43 can be easily bonded to the first covering sheet 41 and the second covering sheet 42 by the wide width parts 471 lying across the plurality of leg elastic members 43.

In the apparatus for manufacturing the absorbent product 1, since the string-like hot melt adhesive is applied onto the second covering sheet 42 along the left-right direction with vibration of the hot melt adhesive in the left-right direction and the vertical direction, the wide width parts can be formed easily. In addition, the adhesive layer elements are formed by spiral spray application, the wide width parts are formed as spiral curves of the hot melt adhesive, and therefore lines of the hot melt adhesive in each wide width part can be densely-arranged. As the result, the leg elastic members 43 and the waist elastic members 44 can be firmly bonded with them. Furthermore, a discharging quantity of the hot melt adhesive from the nozzle is controlled so that the application quantity of the hot melt adhesive per unit length in the left-right direction at the wide width parts is more than that at the narrow width parts, and therefore variation of line widths of the applied hot melt adhesive between the wide width parts and the narrow width parts can be decreased.

Figure 9:
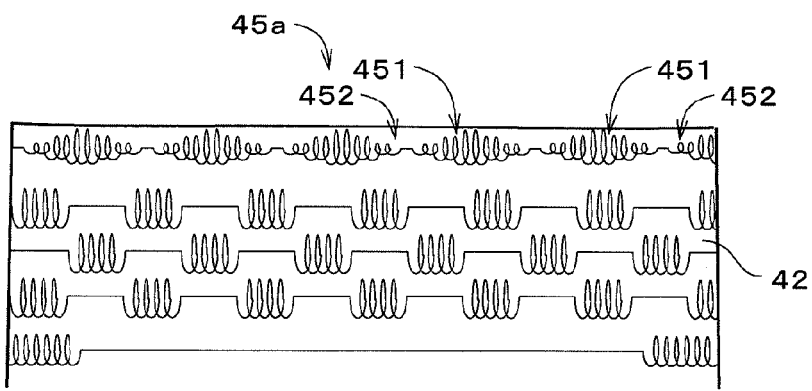
FIG. 9 is a view showing another example of adhesive layer elements.

FIG. 9 is a view showing another preferable example of adhesive layer elements. In FIG. 9, a portion in the vicinity of the upper end of a second covering sheet 42 is drawn as an enlarged view, and a first adhesive layer element 45*a* which has a different shape from the first adhesive layer elements 45 shown in FIGS. 7 and 8 is provided at the upper end of the second covering sheet 42. As shown in FIG. 9, a width of the first adhesive layer element 45*a* at each end portion of each wide width part 451 gradually decreases toward an adjacent narrow width part 452, and the width at each end portion of each narrow width part 452 gradually increases toward an adjacent wide width part 451. In the first adhesive layer element 45*a*, when forming the portion where the width gradually decrease (or increase), a flow rate of gas ejected toward the hot melt adhesive discharged from the nozzle is made to decrease (or increase) gradually. As above, a border between the wide width part 451 and the narrow width part 452 may be unclear, the portion whose width is almost wide (relativelywide) is the wide width part 451, and the portion whose width is almost narrow (relatively-narrow) is the narrow width part 452.

In the absorbent product 1, a thickness of the outer covering sheet 4 at each wide width part of the adhesive layer element is slightly larger than that at each narrow width part. However, since the width of the first adhesive layer element 45a gradually changes at boundary between the wide width part 451 and the narrow width part 452 as described above, hardness variation of the outer covering sheet 4 caused by the first adhesive layer element 45a can be smoothed. As the result, the feel of the absorbent product 1 can be improved and the appearance of the absorbent product 1 can be also improved.

Figure 10:
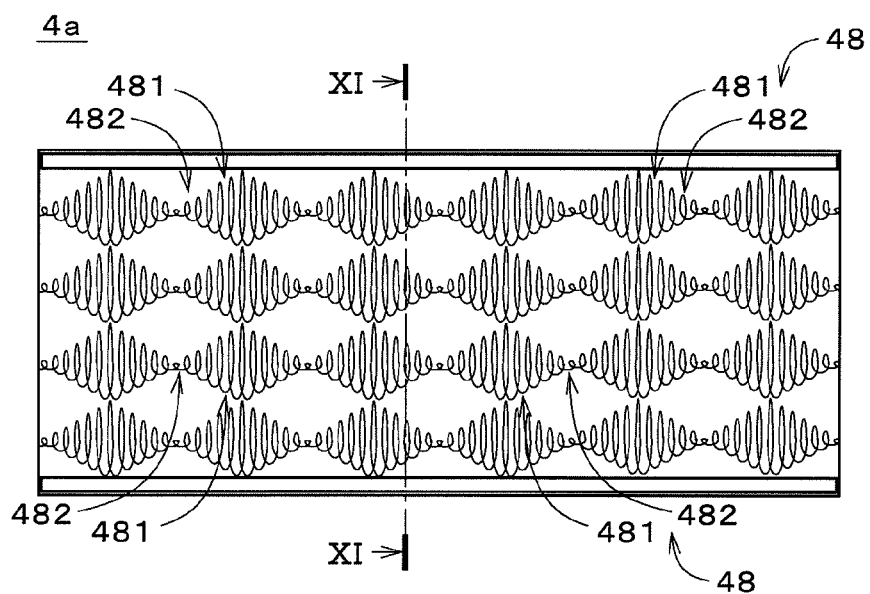
FIG. 10 is a plan view showing a polymer sheet in accordance with a second preferred embodiment.

Next, discussion will be made on a sheet member in accordance with a second preferred embodiment of the present invention. FIG. 10 is a plan view showing a polymer sheet 4a which is a sheet member in accordance with the second preferred embodiment. For example, the polymer sheet 4a is used as an absorbent core of the absorber 20 as a substitute for the absorbent core 22 shown in FIG. 2 when manufacturing a pants-type disposable diaper which is the absorbent product 1 in accordance with the first preferred embodiment. Also the polymer sheet 4a may be used as an absorbent core of a absorbent product such as a tape-type disposable diaper where a portion located on the front side of a wearer and a portion located on the back side are fastened around the waistline of the wearer in wearing the disposal diaper or an auxiliary absorbent pad, or the polymer sheet 4a may be used as a sheet main body of nursing-care sheet which is a absorbent product to be put down under a body of a patient when changing the disposable diaper.

Figure 11:
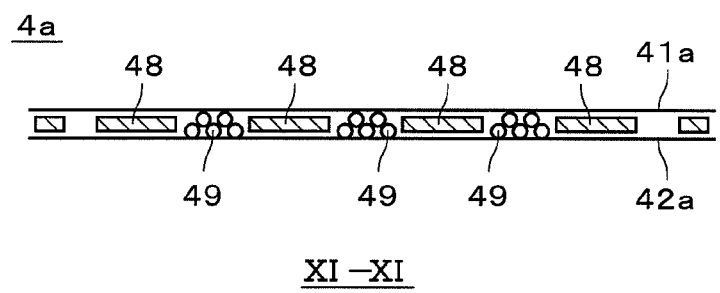
FIG. 11 is a cross-sectional view of the polymer sheet.

FIG. 11 is a cross-sectional view of the polymer sheet 4a taken along a line XI-XI in FIG. 10. As shown in FIG. 11, the polymer sheet 4a has a first sheet 41a and a second sheet 42a each of which is formed of a liquid-pervious nonwoven fabric, plastic film or the like, a plurality of adhesive layer elements 48 (in the present embodiment, four adhesive layer elements 48) for bonding the first sheet 41a to the second sheet 42a, and super absorbent materials 49 which lie between the first sheet 41a and the second sheet 42a, and which are located at respective areas between the plurality of adhesive layer elements 48. Granulated super absorbent polymers (SAP (Super Absorbent Polymer)), super absorbent fibers or the like are used as the super absorbent materials 49, and in the present embodiment, the granulated super absorbent polymers are used. In FIG. 11, the super absorbent materials 49 are enlarged for easy understanding of the drawing. In FIG. 10, the adhesive layer elements 48 are drawn with thin solid lines (the same applies to FIGS. 13 to 17).

The plurality of adhesive layer elements 48 each extending in the left-right direction of FIG. 10 are adjacent to one another in the vertical direction of FIG. 10. Each of the plurality of adhesive layer elements 48 has a plurality of wide width parts 481 and a plurality of narrow width parts 482 each of which are formed by applying the string-like hot melt adhesive in a spiral form extending in the left-right direction. The plurality of wide width parts 481 and the plurality of narrow width parts 482 are arranged in the left-right direction of FIG. 10 alternately and continuously in each adhesive layer element 48.

A width of the adhesive layer element 48 (i.e., the width in the vertical direction of FIG. 10) gradually decreases from the middle of each wide width part 481 in the left-right direction toward the narrow width parts 482 adjacent to the wide width part 481, and the width gradually increases from the middle of each narrow width part 482 in the left-right direction toward the wide width parts 481 adjacent to the narrow width part 482. As above, in each adhesive layer element 48, the width of each wide width part 481 and each narrow width part 482 gradually changes along the left-right direction, and therefore a plurality of approximate rhombus patterns are arranged along the left-right direction.

In the four adhesive layer elements 48 arranged in the vertical direction of FIG. 10, the plurality of wide width parts 481 in one adhesive layer element 48 are adjacent respectively, in the vertical direction, to the plurality of wide width parts 481 in another adhesive layer element 48 which is adjacent to the one adhesive layer element 48. And the plurality of narrow width parts 482 in the one adhesive layer element 48 are adjacent respectively, in the vertical direction, to the plurality of narrow width parts 482 in the another adhesive layer element 48.

Figure 12:
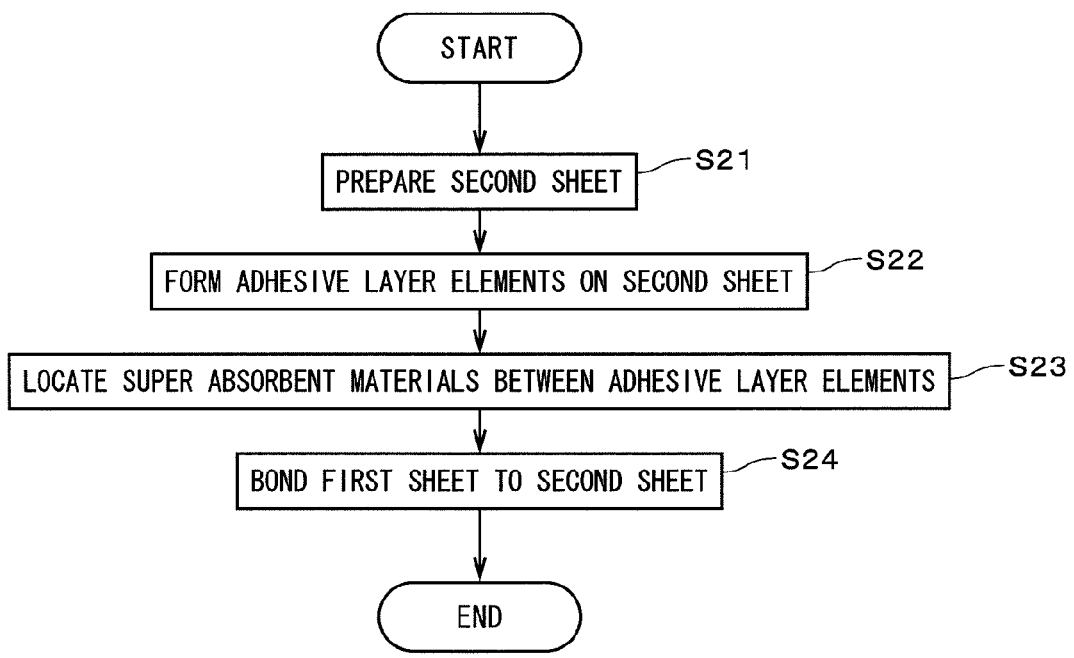
FIG. 12 is a flowchart showing an operation flow for manufacturing the polymer sheet.

FIG. 12 is a flowchart showing an operation flow for manufacturing the polymer sheet 4a. In the manufacture of the polymer sheet 4a, first, the second sheet 42a shown in FIG. 11 is prepared (Step S21), and the plurality of adhesive layer elements 48 are formed on the second sheet 42a (Step S22). In formation of the wide width parts 481 and the narrow width parts 482 of each adhesive layer element 48, gradually increasing a flow rate of gas ejected toward the hot melt adhesive discharged from the nozzle and gradually decreasing the flow rate are repeated continuously.

Therefore, the string-like hot melt adhesive is applied onto the second sheet 42a along the left-right direction of FIG. 10 while the hot melt adhesive is vibrated in the left-right direction and the vertical direction with change in the amplitude of the vertical direction (the amplitude in the left-right direction may be also changed), so that the plurality of wide width parts 481 and the plurality of narrow width parts 482 which are continuous in the left-right direction are formed on the second sheet 42a. Although the plurality of adhesive layer elements 48 are formed in almost parallel with one another in the present embodiment, formation of the plurality of adhesive layer elements 48 is not necessarily performed in parallel manner. After one adhesive layer element 48 of the plurality of adhesive layer elements 48 is formed, another adhesive layer element 48 may be formed.

In the formation of the adhesive layer elements 48, an application quantity of the hot melt adhesive per unit length in the left-right direction at the wide width parts 481 is controlled so as to be more than that at the narrow width parts 482 in similar way to the first preferred embodiment. Therefore, a line width of the applied hot melt adhesive is almost uniform at all portions of the wide width parts 481 and the narrow width parts 482.

After the formation of the adhesive layer elements 48 is finished, the super absorbent materials 49 are located at an area between each two adhesive layer elements 48 adjacent to each other as shown in FIG. 11 (Step S23). After that, the first sheet 41a is bonded to the second sheet 42a with the four adhesive layer elements 48 (Step S24).

As described above, in the polymer sheet 4a, each adhesive layer element 48 comprises the wide width parts 481 and the narrow width parts 482 which are continuous with the wide width parts 481, respectively, and therefore the hot melt adhesive can be stably discharged across the entire length of the adhesive layer element 48 in similar fashion to the first preferred embodiment. As the result, it is possible to obtain the polymer sheet 4a which is a sheet member having the adhesive layer elements 48 with desired shapes where unevenness is decreased.

In the adhesive layer element 48, since the plurality of wide width parts 481 and the plurality of narrow width parts 482 are arranged in the left-right direction of FIG. 10 alternately and continuously, hardness variation of the polymer sheet 4a caused by the adhesive layer elements 48 can be smoothed in similar fashion to the first preferred embodiment. In addition, since the width of each wide width part 481 and each narrow width part 482 gradually changes along the left-right direction of FIG. 10 and the plurality of approximate rhombus patterns are arranged along the left-right direction, thickness variation (or thickness difference) of the polymer sheet 4a caused by the adhesive layer elements 48 can be further reduced. As the result, the feel and the appearance of the absorbent product 1 can be improved.

The plurality of adhesive layer elements 48 which are adjacent to one another in the vertical direction of FIG. 10 are provided in the polymer sheet 4a, the wide width parts 481 in one adhesive layer element 48 of two adhesive layer elements 48 adjacent each other are adjacent respectively, in the vertical direction, to the wide width parts 481 in the other adhesive layer element 48, and the narrow width parts 482 in the one adhesive layer element 48 are adjacent respectively, in the vertical direction, to the narrow width parts 482 in the other adhesive layer element 48. Therefore, in the polymer sheet 4a, approximate rhombus patterns of the applied hot melt adhesive and approximate rhombus areas where the hot melt adhesive is not applied (the areas are nonexistent areas of adhesive) are located almost evenly. As the result, breathability and softness of the polymer sheet 4a are increased almost uniformly.

In the polymer sheet 4a, the super absorbent materials 49 are located at an area between each two adhesive layer elements 48 adjacent to each other (i.e., the area is parts of the above nonexistent areas of adhesive) with the materials lying between the first sheet 41a and the second sheet 42a, and therefore the super absorbent materials 49 can move within the nonexistent areas of adhesive. Thus, when a wearer puts on the absorbent product where the polymer sheet 4a is used, the super absorbent materials 49 move within the nonexistent areas of adhesive so as to make the polymer sheet 4a along the body of the wearer. As the result, it is possible to easily deform the absorbent product where the polymer sheet 4a is used, so as to fit the body of the wearer.

Figure 13:
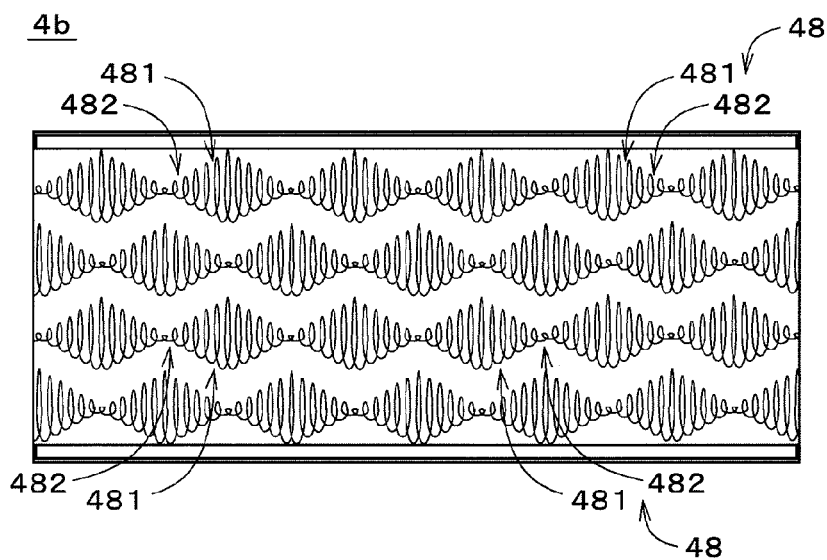
FIG. 13 is a plan view showing another example of polymer sheet.

FIG. 13 is a plan view showing another example of polymer sheet. The polymer sheet 4b shown in FIG. 13 comprises four adhesive layer elements 48 each having the same structure as the adhesive layer elements 48 of the polymer sheet 4a shown in FIG. 10, and these adhesive layer elements 48 are arranged in the vertical direction of FIG. 13. In the polymer sheet 4b, the plurality of wide width parts 481 in one adhesive layer element 48 are adjacent respectively, in the vertical direction, to the plurality of narrow width parts 482 in another adhesive layer element 48 which is adjacent to the one adhesive layer element 48. And the plurality of narrow width parts 482 in the one adhesive layer element 48 are adjacent respectively, in the vertical direction, to the plurality of wide width parts 481 in the another adhesive layer element 48.

In the polymer sheet 4b, since super absorbent materials such as super absorbent polymers or super absorbent fibers are located at respective areas between the plurality of adhesive layer elements 48, it is possible to easily deform the absorbent product where the polymer sheet 4b is used, so as to fit the body of the wearer in similar fashion to the polymer sheet 4a. Also breathability and softness of the polymer sheet 4b are increased almost uniformly.

Though the preferred embodiments of the present invention have been discussed above, the present invention is not limited to the above-discussed preferred embodiments, but allows various variations.

For example, in the manufacture of the absorbent product 1 in accordance with the first preferred embodiment, three leg elastic members 43 are bonded at each of an upper half and a lower half of the middle part of the second covering sheet 42 shown in FIG. 8, however, one or two leg elastic members 43, or leg elastic members 43 more than three may be bonded at each of the upper half and the lower half of the middle part.

In the manufacture of absorbent product 1, there may be the case where during formation of the long narrow width part 472 between two wide width parts 471 of the third adhesive layer element 47 shown in FIG. 7, discharging the hot melt adhesive is temporarily stopped and an area where the hot melt adhesive is not applied is provided at a middle of the narrow width part 472. In this case, each of portions on both sides (left side and right side) of the area is one adhesive layer element comprising two narrow width parts 472 and one wide width part 471 located between them.

In the absorbent product 1, the hot melt adhesive may be applied onto the first covering sheet 41 also. For example, bonding between the first covering sheet 41 and the second covering sheet 42 may be performed with hot melt adhesive applied all over the lower surface of the first covering sheet 41 (i.e., the surface faces the second covering sheet 42) by slit coating or the like, and the first adhesive layer elements 45, the second adhesive layer elements 46 and the third adhesive layer elements 47 on the second covering sheet 42. Applied adhesive other than the first adhesive layer elements 45, the second adhesive layer elements 46 and the third adhesive layer elements 47 may be provided on the second covering sheet 42. For example, the adhesive is applied uniformly on non-application areas between the first adhesive layer elements 45, the second adhesive layer elements 46 and the third adhesive layer elements 47 or on positions overlapping with these adhesive layer elements.

Also in the polymer sheet 4a in accordance with the second preferred embodiment, the hot melt adhesive is applied onto the lower surface of the first sheet 41a (i.e., the surface faces the second sheet 42a) and bonding between the first sheet 41a and the second sheet 42a may be performed with the applied hot melt adhesive and the adhesive layer elements 48 on the second sheet 42a. Applied adhesive other than the adhesive layer elements 48 may be provided on the second sheet 42a. For example, the adhesive is applied uniformly on non-application areas where the adhesive layer elements 48 are not formed or on positions overlapping with the adhesive layer elements 48.

In the polymer sheet 4a, the super absorbent materials 49 are not necessarily located at all the nonexistent areas of adhesive as long as they are located at least at an area between any two adhesive layer elements 48. Also the super absorbent materials 49 may be located on the adhesive layer elements 48. For example, the super absorbent materials 49 are evenly located almost all over the surface of the second sheet 42a.

Figure 14:
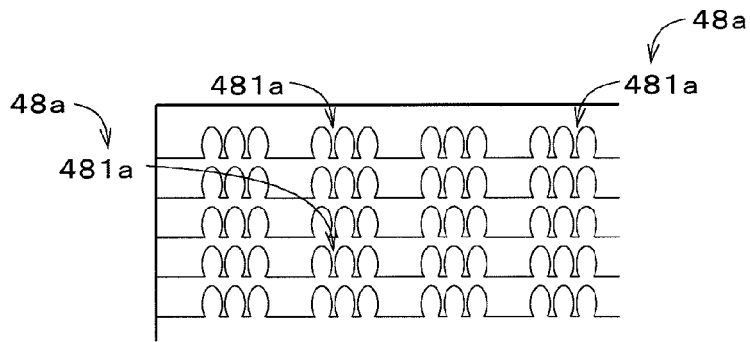
FIGS. 14 to 17 are plan views showing other examples of adhesive layer elements.

Each adhesive layer element of the absorbent product 1 and the polymer sheet 4a is not necessarily formed by spiral spray application, and it may be formed by another application. For example, in the case where a direction in which each adhesive layer element 48a extends is a first direction and a direction orthogonal to the first direction is a second direction, the string-like hot melt adhesive is discharged along the first direction (i.e., with relative movement in the first direction) with vibration of the hot melt adhesive in the first direction and the second direction, and therefore as shown in FIG. 14, the hot melt adhesive is applied in Ω (omega) forms to form a wide width part 481a.

Figure 15:
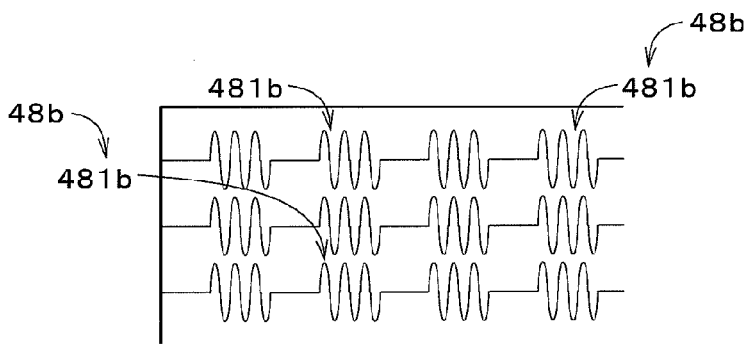
Figure 16:
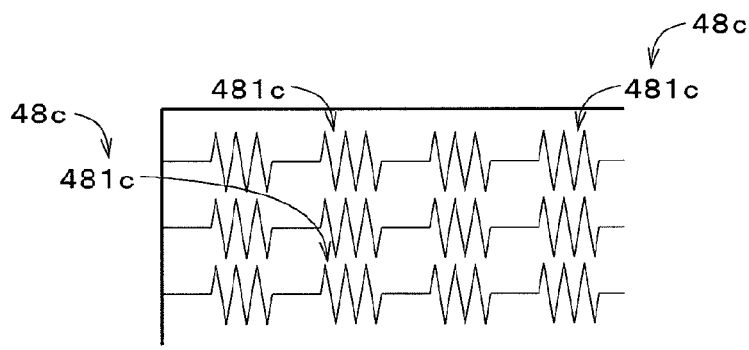
Figure 17:
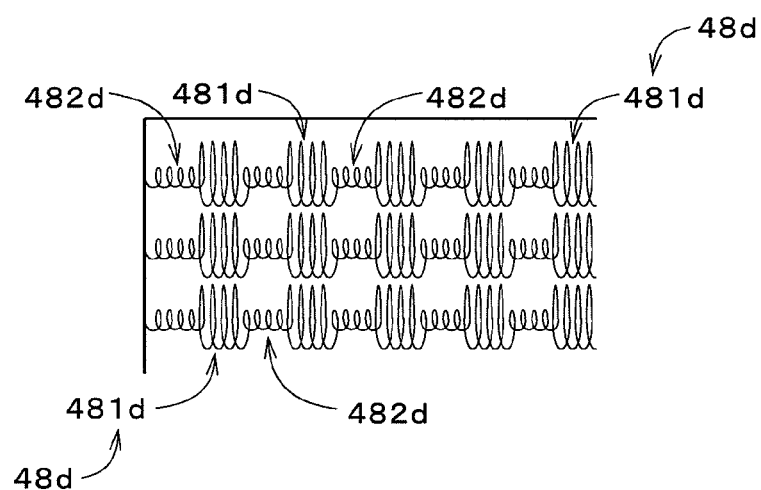

In each of adhesive layer elements 48b, 48c shown respectively in FIGS. 15 and 16, the string-like hot melt adhesive is discharged along the first direction with vibration of the hot melt adhesive in the second direction, and therefore the hot melt adhesive is applied in a sinusoidal form or zigzag form to form a wide width part 481b, 481c. As above, in the formation of adhesive layer element, the wide width part is formed by applying the string-like hot melt adhesive along the first direction with vibration of the hot melt adhesive at least in the second direction. In adhesive layer elements 48d shown in FIG. 17, narrow width parts 482d which are narrower in the second direction than wide width parts 481d are formed by applying the string-like hot melt adhesive along the first direction with vibration of the hot melt adhesive in the first direction and the second direction in similar fashion to the wide width parts 481d.

In formation of each adhesive layer element of the absorbent product 1 and the polymer sheet 4a, an application quantity of the hot melt adhesive per unit length at the wide width parts is not necessarily controlled so as to be more than that at the narrow width parts (i.e., the application quantity of the hot melt adhesive per the unit length at the narrow width parts). For example, the application quantity of the hot melt adhesive per the unit length may be uniform across the entire length of the adhesive layer element. In addition, adhesive to form each adhesive layer element is not limited to the hot melt adhesive, and the above adhesive layer elements may be formed with another type of adhesive.

In the above preferred embodiments, the outer covering sheet 4 of double-layered structure comprising the first covering sheet 41 and the second covering sheet 42, and the polymer sheet 4a of double-layered structure comprising the first sheet 41a and the second sheet 42a are exemplified as a sheet member in accordance with the present invention, however the sheet member need not have the double-layered structure, and the sheet member may be used as various members other than the outer covering sheet 4 and the polymer sheet 4a for manufacturing various absorbent products.

Figure 18:
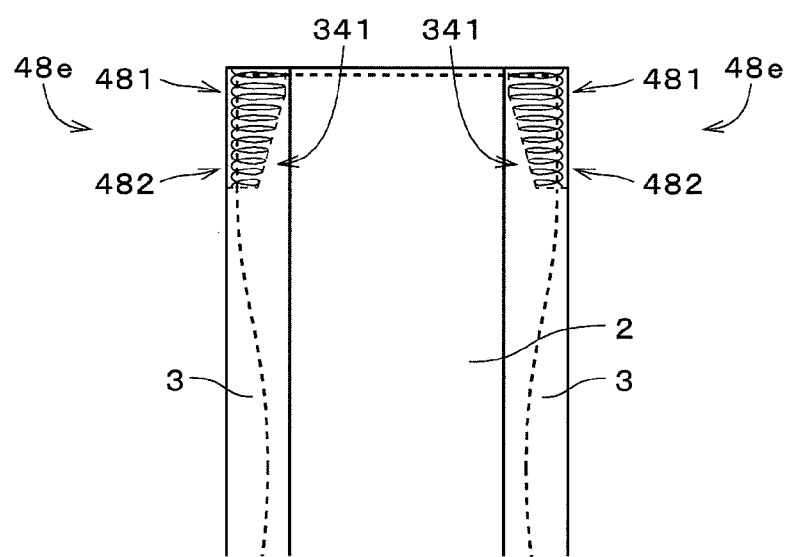
FIG. 18 is a plan view showing another example of sheet member.

For example, as shown in FIG. 18, the sheet member is bonded on each side portion of the main body part 2 to become the side sheet 3 in the manufacture of the absorbent product 1 in accordance with the first preferred embodiment. As shown in FIG. 18, an adhesive layer element 48e extending in the longitudinal direction of the main body part 2 is formed with the hot melt adhesive at the side wall end part 341 of the side sheet 3, and the adhesive layer element 48e has a wide width part 481 and a narrow width part 482 which is continuous with the wide width part 481 in the longitudinal direction. The side wall end part 341 of the side sheet 3 is bonded on the main body part 2 with the adhesive layer element 48e. Therefore, it is possible to make a portion of the side sheet 3 be standing toward the wearer's side at the side wall end part 341 and to gradually lower the height of the standing portion toward the end of the main body part 2 in the longitudinal direction.

In the apparatus for manufacturing the absorbent product 1 in accordance with the first preferred embodiment, an adhesive layer element having a wide width part and a narrow width part may be utilized for bonding between the absorber 20 and the outer covering sheet 4. In the case where the adhesive layer element is formed on the outer covering sheet 4, the outer covering sheet 4 or the first covering sheet 41 is treated as a sheet of a sheet member in accordance with the present invention. On the other hand, in the case where the adhesive layer element is formed on the lower surface of the absorber 20, the absorber 20 or the back sheet 23 of the main body part 2 is treated as the sheet of the sheet member. Also the above adhesive layer element may be used for bonding between the end holding sheet 5 and the outer covering sheet 4. In this case, the outer covering sheet 4 or the first covering sheet 41, or the end holding sheet 5 is treated as the sheet of the sheet member.

While the invention has been shown and described in detail, the foregoing description is in all aspects illustrative and not restrictive. It is therefore understood that numerous modifications and variations can be devised without departing from the scope of the invention. This application claims priority benefit under 35 U.S.C. Section 119 of Japanese Patent Application No. 2009-220728 filed in the Japan Patent Office on Sep. 25, 2009, the entire disclosure of which is incorporated herein by reference.

REFERENCE SIGNS LIST 1 absorbent product
3 side sheet
4 outer covering sheet
4a, 4b polymer sheet
5 end holding sheet
22 absorbent core
23 back sheet
41 first covering sheet
41a first sheet
42 second covering sheet
42a second sheet
43 leg elastic member
44 waist elastic member
45, 45a first adhesive layer element
46 second adhesive layer element
47 third adhesive layer element
48, 48a to 48e adhesive layer element
49 super absorbent materials
451, 461, 471, 481, 481a to 481d wide width part
452, 462, 472, 482, 482d narrow width part
S11 to S14, S21 to S24, S121 to S123 step

The invention claimed is:

1. A method of manufacturing a sheet member to be used for manufacturing an absorbent product, the method comprising:
    forming a first adhesive layer element on a sheet such that the first adhesive layer element extends in a first direction, including:
    a) forming a wide width part by applying string-like adhesive onto the sheet along the first direction with vibration of the adhesive in a second direction orthogonal to the first direction; and
    b) forming a narrow width part which is narrower than the wide width part, by applying string-like the adhesive onto the sheet along the first direction with or without vibration of the adhesive in the second direction, the narrow width part being continuous with the wide width part,
    wherein a width of the first adhesive layer element gradually changes at a boundary between the wide width part and the narrow width part.

2. The method of claim 1, wherein said forming the wide with part and said forming the narrow width part are performed alternately and continuously.

3. The method of claim 2, further comprising:
    forming a second adhesive layer element which has the same structure as the first adhesive layer element, simultaneously with or after said forming the first adhesive layer element, the second adhesive layer element extending in the first direction and being adjacent to the first adhesive layer element in the second direction.

4. The method of claim 3, further comprising:

after said forming the first adhesive layer element and said forming the second adhesive layer element, providing super absorbent polymers or super absorbent fibers at least at an area between the first adhesive layer element and the second adhesive layer element; and after said providing the super absorbent polymers or the super absorbent fibers, bonding another sheet to the sheet with the first adhesive layer element and the second adhesive layer element.

5. The method of claim 1, further comprising:

bonding an elastic member to the sheet with the first adhesive layer element; and bonding another sheet to the sheet with the first adhesive layer element, simultaneously with or after said bonding the elastic member.

6. The method of claim 1, further comprising:

controlling an application quantity of the adhesive during said forming the first adhesive layer element such that the application quantity of the adhesive per unit length in the first direction at the wide width part is more than the application quantity of the adhesive per unit length in the first direction at the narrow width part.

7. The method of claim 1, wherein the first adhesive layer element has an oscillating, sinusoidal, or zigzag form and a width of the first adhesive layer element in the second direction is an amplitude of the oscillating, sinusoidal, or zigzag form.

8. The method of claim 1, wherein the first adhesive layer element has a oscillating, sinusoidal, or zigzag form and a width of the first adhesive layer element in the second direction is an amplitude of the oscillating, sinusoidal, or zigzag form, and wherein the width of the first adhesive layer element has a gradual change at boundary between said wide width part and said narrow width part, and the gradual change includes multiple oscillating, sinusoidal, or zigzag forms of incrementally smaller amplitudes.

9. The method of claim 1, wherein said forming the first adhesive layer element includes forming a plurality of wide width parts and a plurality of narrow width parts in alternating order in the first direction, wherein the first adhesive layer element has a oscillating, sinusoidal, or zigzag form and a width of the first adhesive layer element in the second direction is an amplitude of the oscillating, sinusoidal, or zigzag form, and wherein the width of said first adhesive layer element has a gradual change at boundary between each wide width part and each narrow width part, and the gradual change includes multiple oscillating, sinusoidal, or zigzag forms of incrementally smaller amplitudes.

10. A method comprising:

forming a first adhesive layer element on a first sheet such that the first adhesive layer element extends in a first direction, including:

a) forming a wide width part by applying string-like adhesive onto the first sheet along the first direction with vibration of the adhesive in a second direction orthogonal to the first direction; and b) forming a narrow width part which is narrower than the wide width part, by applying string-like the adhesive onto the first sheet along the first direction with or without vibration of the adhesive in the second direction, the narrow width part being continuous with the wide width part;

bonding an elastic member to the first sheet with the first adhesive layer element;

bonding a second sheet to the first sheet with the first adhesive layer element with an absorbent core disposed between the first sheet and the second sheet;

forming the first sheet, the second sheet, the absorbent core, and the elastic member into an absorbent product having a waist opening and two leg openings.

11. The method of claim 10, further comprising:

forming a second adhesive layer element which has the same structure as the first adhesive layer element, simultaneously with or after said forming the first adhesive layer element, the second adhesive layer element extending in the first direction and being adjacent to the first adhesive layer element in the second direction.

12. The method of claim 10, further comprising:

after said forming the first adhesive layer element and said forming the second adhesive layer element, providing super absorbent polymers or super absorbent fibers at least at an area between the first adhesive layer element and the second adhesive layer element; and after said providing the super absorbent polymers or the super absorbent fibers, bonding another sheet to the sheet with the first adhesive layer element and the second adhesive layer element.

13. The method of claim 10, further comprising:

controlling an application quantity of the adhesive during said forming the first adhesive layer element such that the application quantity of the adhesive per unit length in the first direction at the wide width part is more than the application quantity of the adhesive per unit length in the first direction at the narrow width part.

14. The method of claim 10, wherein the first adhesive layer element has an oscillating, sinusoidal, or zigzag form and a width of the first adhesive layer element in the second direction is an amplitude of the oscillating, sinusoidal, or zigzag form.

15. The method of claim 10, wherein the first adhesive layer element has a oscillating, sinusoidal, or zigzag form and a width of the first adhesive layer element in the second direction is an amplitude of the oscillating, sinusoidal, or zigzag form, and wherein the width of said first adhesive layer element has a gradual change at boundary between said wide width part and said narrow width part, and the gradual change includes multiple oscillating, sinusoidal, or zigzag forms of incrementally smaller amplitudes.

16. The method of claim 10, wherein said forming the first adhesive layer element includes forming a plurality of wide width parts and a plurality of narrow width parts in alternating order in the first direction.

17. A method comprising:

forming a first adhesive layer element on a first sheet such that the first adhesive layer element extends in a first direction, including:

a) forming a wide width part by applying string-like adhesive onto the first sheet along the first direction with vibration of the adhesive in a second direction orthogonal to the first direction; and b) forming a narrow width part which is narrower than the wide width part, by applying string-like the adhesive onto the first sheet along the first direction with or without vibration of the adhesive in the second direction, the narrow width part being continuous with the wide width part;

bonding an elastic member to the first sheet with the first adhesive layer element;

bonding a second sheet to the first sheet with the first adhesive layer element with an absorbent core disposed between the first sheet and the second sheet; and forming the first sheet, the second sheet, the absorbent core, and the elastic member into an absorbent product having a waist opening and two leg openings, wherein said forming the first adhesive layer element includes forming a plurality of wide width parts and a plurality of narrow width parts in alternating order in the first direction, wherein the first adhesive layer element has a oscillating, sinusoidal, or zigzag form and a width of the first adhesive layer element in the second direction is an amplitude of the oscillating, sinusoidal, or zigzag form, and wherein the width of said first adhesive layer element has a gradual change at boundary between each wide width part and each narrow width part, and the gradual change includes multiple oscillating, sinusoidal, or zigzag forms of incrementally smaller amplitudes.

* * * * *